(12) United States Patent
Nabutovsky et al.

(10) Patent No.: US 9,174,052 B1
(45) Date of Patent: Nov. 3, 2015

(54) METHODS AND SYSTEMS FOR CONTROLLING STIMULATION IN PADDLE LEAD BASED ON LOCAL IMPEDANCES

(71) Applicant: Pacesetter, Inc., Sunnyvale, CA (US)

(72) Inventors: Yelena Nabutovsky, Mountain View, CA (US); Fujian Qu, San Jose, CA (US); Lalit Venkatesan, Prosper, TX (US); Kyungmoo Ryu, Palmdale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/328,499

(22) Filed: Jul. 10, 2014

(51) Int. Cl.
*A61N 1/00* (2006.01)
*A61N 1/36* (2006.01)
*A61N 1/05* (2006.01)

(52) U.S. Cl.
CPC .......... *A61N 1/36128* (2013.01); *A61N 1/0553* (2013.01); *A61N 1/36071* (2013.01); *A61N 1/36142* (2013.01); *A61N 1/36192* (2013.01)

(58) Field of Classification Search
CPC ............... A61B 5/053; A61B 1/36185; A61B 1/36139; A61B 1/08; A61B 1/0529; A61B 1/0551
See application file for complete search history.

(56) References Cited

U.S. PATENT DOCUMENTS

| | | | |
|---|---|---|---|
| 7,149,573 B2* | 12/2006 | Wang | 600/547 |
| 2013/0006324 A1* | 1/2013 | Bradley | 607/45 |
| 2014/0135870 A1* | 5/2014 | Carlson | A61N 1/0529 607/45 |
| 2014/0296941 A1* | 10/2014 | King et al. | 607/62 |
| 2015/0112321 A1* | 4/2015 | Cadouri | 606/34 |

* cited by examiner

*Primary Examiner* — Robert N Wieland
(74) *Attorney, Agent, or Firm* — Theresa A. Raymer (57) ABSTRACT

The present disclosure provides systems and methods for neurostimulation. The method includes applying electrical stimulation to a patient using a paddle lead that includes a plurality of electrodes, acquiring local impedances associated with at least some of the plurality of electrodes, wherein the local impedances are indicative of electrode-tissue contact and effectiveness of the electrical stimulation, transmitting the local impedances data to a computing device, and processing the local impedances data using the computing device to adjust the amplitude of stimulations and electrode configurations, and monitor electrode-tissue contact status over time.

20 Claims, 7 Drawing Sheets

METHODS AND SYSTEMS FOR CONTROLLING STIMULATION IN PADDLE LEAD BASED ON LOCAL IMPEDANCES

FIELD OF THE DISCLOSURE

The present disclosure relates generally to neurostimulation methods and systems, and more particularly to controlling stimulation in a paddle lead based on local impedances.

BACKGROUND ART

Application of electrical stimulation to spinal nerve roots, spinal cord, and other nerve bundles for the purpose of chronic pain control has been actively practiced for some time. While a precise understanding of the interaction between applied electrical stimulation and the nervous tissue is not fully appreciated, it has been shown that such application can effectively mask certain types of pain transmitted from regions of the body associated with the stimulated nerve tissue. Specifically, applying electrical stimulation to regions of the spinal cord associated with regions of the body afflicted with chronic pain can induce "paresthesia" (a subjective sensation of numbness or tingling) in the afflicted regions and therefore effectively mask the transmission of chronic pain sensations to the brain.

Each exterior region, or each dermatome, of the human body is associated with a particular spinal nerve root at a particular longitudinal spinal position. The head and neck regions are associated with C2-C8, the back regions extend from C2-S3, the central diaphragm is associated with spinal nerve roots between C3 and C5, the upper extremities correspond to C5 and T1, the thoracic wall extends from T1 to T11, the peripheral diaphragm is between T6 and T1 the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. For example, to address chronic pain sensations that commonly focus on the lower back and lower extremities using conventional techniques, a specific energy field is typically applied to a region between vertebrae levels T8 and T12. The specific energy field often stimulates a number of nerve fibers and structures of the spinal cord. By applying energy in this manner, the patient commonly experiences paresthesia over a relatively wide region of the patient's body from the lower back to the lower extremities.

Positioning of applied electrical stimulation relative to a physiological midline is also important. Nerve fibers extend between the brain and a nerve root along the same side of the dorsal column that the peripheral areas the fibers represent. Pain that is concentrated on only one side of the body is "unilateral" in nature. To address unilateral pain, electrical stimulation is applied to neural structures on the side of a dorsal column that directly corresponds to a side of the body subject to pain. Pain that is present on both sides of a patient is "bilateral". Accordingly, bilateral pain is addressed through application of electrical stimulation along both sides of the column and/or along a patient's physiological midline.

Figure 1A:
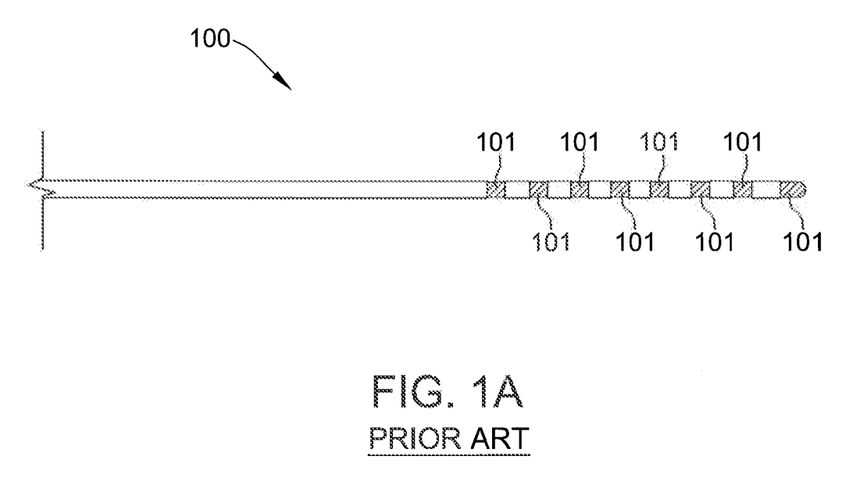
FIG. 1A is a schematic diagram of a conventional percutaneous lead.

Percutaneous leads and laminotomy leads are the two most common types of lead designs that provide conductors to deliver stimulation pulses from an implantable pulse generator (IPG) to distal electrodes adjacent to the pertinent nerve tissue. Example commercially available stimulation leads include the QUATTRODE™ OCTRODE™, AXXESS™, LAMITRODE™, TRIPOLE™, EXCLAIM™, and PENTA™ stimulation leads from St. Jude Medical, Inc. As shown in FIG. 1A, a conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

Figure 1B:
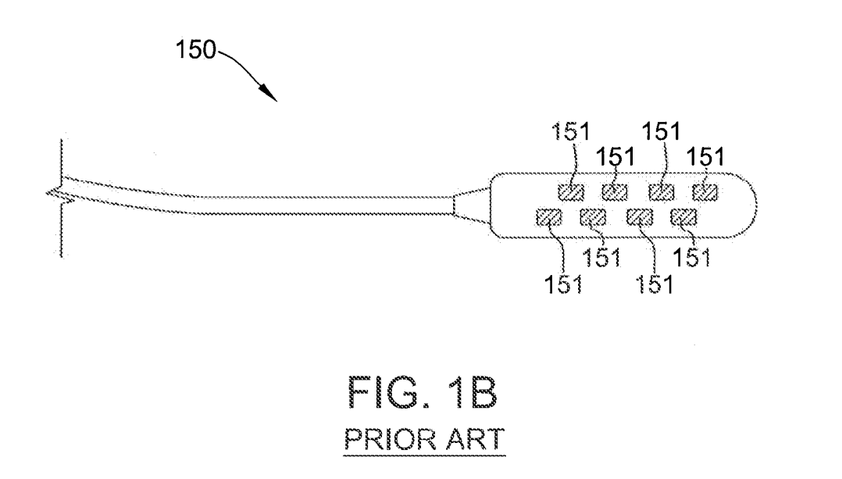
FIG. 1B is a schematic diagram of a conventional paddle lead.

As shown in FIG. 1B, a conventional laminotomy or paddle lead 150 has a paddle configuration and typically possesses a plurality of electrodes 151 (commonly, two, four, eight, or sixteen) arranged in columns. Due to their dimensions and physical characteristics, conventional laminotomy leads may require a surgical procedure (a partial laminectomy) for implantation. Multi-column laminotomy leads enable more reliable positioning of a plurality of electrodes as compared to percutaneous leads. Also, laminotomy leads offer a more stable platform that tends to migrate less after implantation and that is capable of being sutured in place. Laminotomy leads also create unidirectional electrical stimulation and, hence, can be used in a more electrically efficient manner than at least some known percutaneous leads.

Depending on the stimulation parameters, IPGs may have a relatively short battery-life. Further, replacement of an IPG is an invasive procedure that involves placing a new IPG in the same subcutaneous pocket that contained the original IPG. Moreover, patients who receive these devices may be middle-aged, requiring multiple IPG replacements during their lifetime. Accordingly, it is desirable to improve the longevity of these devices, for example, by reducing the power consumption of these devices.

BRIEF SUMMARY OF THE DISCLOSURE

In one embodiment, the present disclosure is directed to a system for applying neurostimulation to a patient, the system including a paddle lead including a plurality of electrodes, and an implantable pulse generator (IPG) electrically coupled to the paddle lead. The IPG is configured to calculate, using a processing device, an impedance for each electrode in a set of electrodes on the paddle lead, determine, using the processing device, at least one electrode in the set of electrodes having a lowest impedance within a predefined range, and automatically cause the paddle lead to perform stimulation using the at least one electrode. The system further includes a programmer device communicatively coupled to the IPG and configured to control operation of the IPG.

In another embodiment, the present disclosure is directed to an implantable pulse generator (IPG) configured to be electrically coupled to a paddle lead that includes a plurality of electrodes. The IPG includes a memory device, and a processing device communicatively coupled to the memory device, the processing device configured to calculate an impedance for each electrode in a set of electrodes on the paddle lead, determine at least one electrode in the set of electrodes having a lowest impedance within a predefined range, and automatically cause the paddle lead to perform stimulation using the at least one electrode.

In another embodiment, the present disclosure is directed to a method for applying neurostimulation to a patient, the method including electrically coupling a paddle lead to an implantable pulse generator (IPG), wherein the paddle lead includes a plurality of electrodes, calculating, using a processing device, an impedance for each electrode in a set of electrodes on the paddle, determining, using the processing device, at least one electrode in the set of electrodes having a lowest impedance within a predefined range, and automatically causing the paddle lead to perform stimulation using the at least one electrode.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for controlling stimulation in a paddle lead based on local impedances. Local impedances are calculated for a set of electrodes on the paddle lead. The calculated local impedances may be analyzed to modify stimulation parameters, generate alerts, and/or display pertinent information to a user.

I. DEFINITIONS

Unless defined otherwise, technical and scientific terms used herein have the same meaning as commonly understood by one of ordinary skill in the art to which this disclosure belongs. For purposes of the present disclosure, the following terms are defined below.

As used herein, the use of the word "a" or "an" when used in conjunction with the term "comprising" in the claims and/or the specification may mean "one", but it is also consistent with the meaning of "one or more," "at least one", and "one or more than one". Still further, the terms "having", "including", "containing" and "comprising" are interchangeable and one of skill in the art is cognizant that these terms are open-ended terms. Some embodiments may consist of or consist essentially of one or more elements, method steps, and/or methods of the disclosure. It is contemplated that any method or composition described herein can be implemented with respect to any other method or composition described herein.

As used herein, the use of the term "dorsal column" refers to conducting pathways in the spinal cord that are located in the dorsal portion of the spinal cord between the posterior horns, and which includes afferent somatosensory neurons. The dorsal column is also known as the posterior funiculus.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T1 nerve root leaves the spinal cord myelum at an area located behind vertebral body T8-T9 but leaves the bony spine between T11 and T12.

As used herein the term "chronic pain" refers to a persistent state of pain experienced for a substantial amount of time (e.g., longer than three months).

As used herein the term "complex regional pain syndrome" or "CRPS" refers to painful conditions that usually affect the distal part of an upper or lower extremity and are associated with characteristic clinical phenomena. CRPS is divided into two subtypes CRPS Type I and CRPS Type II. Generally, the clinical characteristics of Type I are the same as seen in Type II. The central difference between Type I and Type II is that Type II typically occurs following a sensory nerve injury whereas Type I occurs in the absence of any known nerve injury.

II. ORGANIZATION OF THE NERVOUS SYSTEM

The nervous system includes two general components, the central nervous system, which is composed of the brain and the spinal cord, and the peripheral nervous system, which is composed of ganglia or dorsal root ganglia and the peripheral nerves that lie outside the brain and the spinal cord. Those of skill in the art will appreciate that the components of the nervous system may be linguistically separated and categorized, but functionally they are interconnected and interactive.

Figure 2:
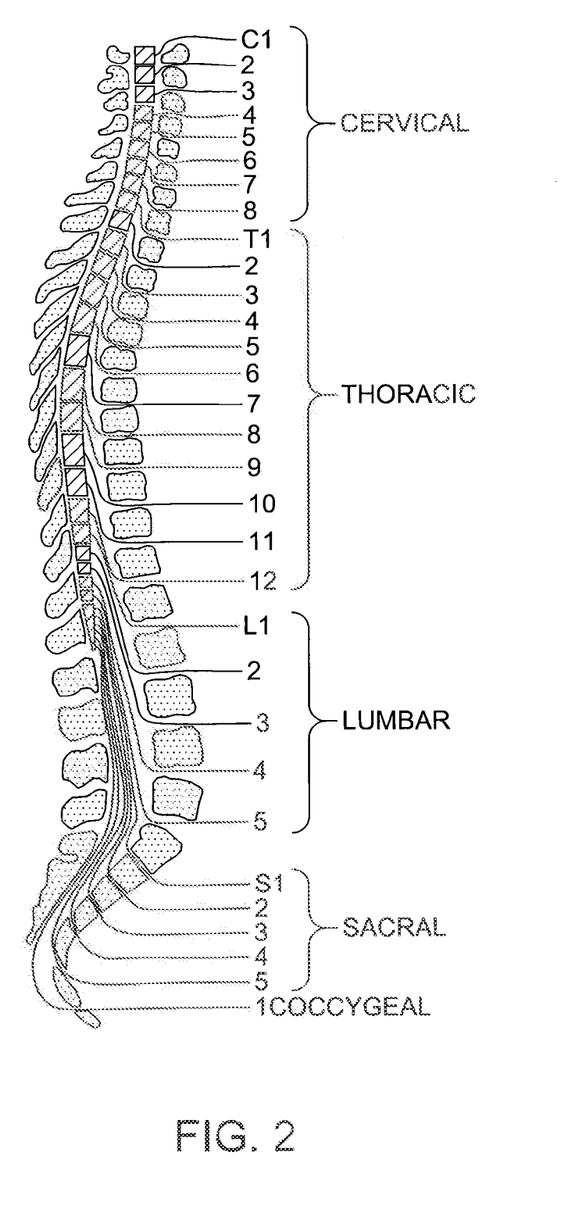
FIG. 2 is a schematic diagram of the spinal cord and the nerve roots in relation to the vertebral spinal canal.

The central nervous system includes the brain and spinal cord, which together function as the principal integrator of sensory input and motor output. In general terms, the brain consists of the cerebrum (cerebral hemispheres and the diencephalons), the brainstem (midbrain, pons, and medulla), and the cerebellum. The spinal cord is organized into segments, for example, there are 8 cervical (C1-C8), 12 thoracic (T1-T12), 5 lumbar (L1-L5), 5 sacral (S1-S5), and cocygeal (Co1) spinal segments. In adults, the spinal cord typically ends at the level of the L1 or L2 vertebral bones. As shown in FIG. 2, the nerve roots travel downward to reach their exit points at the appropriate levels. Left and right sensory and motor nerve roots arise from each segment of the spinal cord except for the C1 and Co1 segments, which have no sensory roots. Associated sensory and motor nerve roots fuse to form a single mixed spinal nerve for each segment. The mixed spinal nerves further fuse and intermingle peripherally to form plexuses and nerve branches.

The peripheral nervous system is divided into the autonomic system (parasympathetic and sympathetic), the somatic system, and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

II. STIMULATION LEADS AND SYSTEMS

Figure 3:
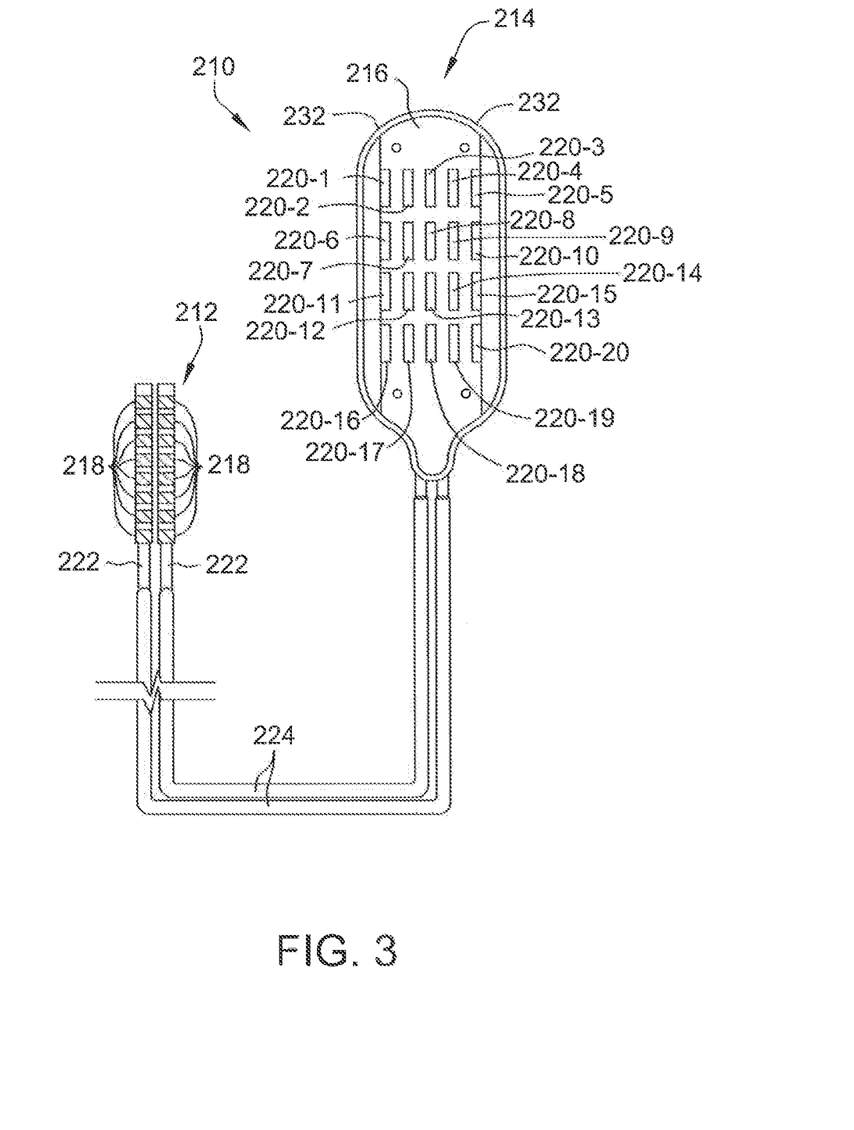
FIG. 3 is a schematic diagram of a paddle lead according to one embodiment.

FIG. 3 is a schematic diagram of a paddle lead 210 according to one embodiment. Paddle lead 210 includes a proximal end 212 and a distal end 214. Proximal end 212 includes a plurality of electrically conductive terminals 218. Distal end 214 includes a plurality of electrically conductive electrodes 220 (labeled 220-1 through 220-20) arranged within a substantially flat, thin paddle 216. Electrodes 220 are mutually separated by insulative material of paddle 216. For a paddle structure adapted for implantation within a cervical vertebral level, electrodes 220 are may be spaced apart 1.5 mm laterally and 2.5 mm longitudinally. For a paddle adapted for implantation within a thoracic vertebral level, electrodes 220 may be spaced apart by 1.0 mm laterally and 2 mm or 3 mm longitudinally. Conductors 222 (which are embedded within the insulative material of the lead body) electrically connect electrodes 220 to terminals 218.

In the embodiment shown in FIG. 3, paddle 216 includes five columns and four rows of electrodes 220 arranged in a grid configuration, for a total of twenty electrodes 220. Alternative numbers of columns and rows may be employed. For example, in some embodiments, thirty-two or more electrodes are distributed into multiple rows and multiple columns. Also, every row need not contain the same number of columns. For example, a number of rows can include a "tripole" design having three columns of electrodes while additional rows can include five or more columns of electrodes to enable a greater amount of electrical stimulation resolution. The multiple columns of electrodes 220 enable lateral control of the applied electrical stimulation to stimulate the exact lateral position of the pertinent nerve fiber(s), as described herein.

Specifically, it may be desirable to selectively stimulate a given dorsal column fiber that is associated with an afflicted region of the patient's body without affecting other regions of the patient's body. The multiple columns of paddles according to representative embodiments provide sufficient resolution to relatively finely control the stimulation of one or several specific fibers, as described herein. Additionally, the multiple columns provide a degree of positional tolerance during the surgical placement of paddle 216 within the epidural space, as any one of the columns may be used to stimulate the pertinent nerve fiber(s). Also, if paddle 216 is displaced relative to the pertinent nerve fibers subsequent to implantation (e.g., due to lead migration), the stimulation pattern applied by a pulse generator can be shifted between columns to compensate for the displacement.

The multiple rows of electrodes 220 enable multiple pain locations to be treated with a single implanted lead. Specifically, a first row can be used to treat a first pain complaint (e.g., pain in the lower extremities) and a second row can be used to treat a second pain location (e.g., post-laminectomy pain in the back). Furthermore, by separating the first and second rows by one or more "buffer" rows of high-impedance electrodes 220, the stimulation in the first and second rows may occur on a substantially independent basis. Specifically, anodes in the second row will have relatively minimal effect on the field distribution generated by cathodes in the first row.

In some embodiments, paddle lead 210 can be implanted within a patient such that electrodes 220 are positioned within the cervical or thoracic spinal levels. After implantation, an electrode combination on a first row of electrodes 220 can be determined that is effective for a first pain location with minimal effects on other regions of the body. The first pain location can be addressed by stimulating a specific dorsal column fiber due to the relatively fine electrical stimulation resolution achievable by the multiple columns. Then, another electrode combination on a second row of electrodes 220 can be determined for a second pain location with minimal effects on other regions of the body. The second pain location could be addressed by stimulating another dorsal column fiber as an example. After the determination of the appropriate electrodes 220 for stimulation, a patient's implantable pulse generator (IPG) can be programmed to deliver pulses using the first and second rows according to the determined electrode combinations.

When determining the appropriate electrode configurations, the selection of electrodes 220 to function as anodes can often facilitate isolation of the applied electrical stimulation to desired fibers and other neural structures. Specifically, the selection of an electrode 220 to function as an anode at a position adjacent to another electrode 220 functioning as a cathode causes the resulting electron/ion flow to be limited to tissues immediately surrounding the two electrodes 220. By alternating through a plurality of anode/cathode combinations, as described herein, it is possible to improve resolution in the stimulation of dorsal column fibers. Also, it is possible to confine the applied electrical stimulation to or away from a periphery of paddle 216.

The operation of anodes can also be used to hyperpolarize neural tissue. Depending on the stimulation amplitude and the proximity of an anode to the pertinent neural tissue, the hyperpolarization can be used to prevent selected neural tissue from propagating action potentials. The hyperpolarization can also be used to prevent an adjacent cathode from initiating propagation of an action potential beginning at the selected neural tissue.

Multiple columns of electrodes 220 also enable lateral "steering" of the electrical stimulation using a single channel pulse generator. A single channel pulse generator refers to a pulse generator that provides an equal magnitude pulse to each active electrode 220 at a given time. Specifically, each electrode 220 is either "active" (i.e., it is coupled to the pulse generator output during pulse generation by a suitable gate or switch) or "inactive" (i.e., the gate or switch does not couple the electrode to the pulse generator output). Each "active" electrode 220 experiences the same amplitude; only the polarity varies depending upon whether electrode 220 is set as a cathode or anode as defined by positions of respective gates and/or switches.

The steering of the electrical stimulation occurs by selecting appropriate states for electrodes 220. Depending upon the desired neural tissue to be stimulated, it may be beneficial to confine the electrical stimulation along the periphery of paddle 216. Confinement of the electrical stimulation along the periphery can be accomplished by setting electrode 220-1 to function as a cathode and setting electrode 220-2 to function as an anode. Because the electrical stimulation will generally be confined between these two electrodes 220 during stimulation pulses, only nerve fibers within the adjacent area will be stimulated. Generally speaking, nerve fibers past electrode 220-2 would not be stimulated when a pulse is delivered via electrode 220-1 due to the anodalhyperpolarizing effect.

Conductors 222 are carried in sheaths 224. In some embodiments, each sheath 224 carries eight conductors 222. With only two sheaths 224 with eight conductors each, there would only be sixteen conductors 222. To accommodate the lower number of conductors 222 than electrodes 220, multiple electrodes 220 may be coupled to the same conductor 222 (and, hence, to a common terminal 218). In the example embodiment, electrodes 220-1 and 220-6 are coupled to a common conductor 222, electrodes 220-5 and 220-10 are coupled to a common conductor 222, electrodes 220-11 and 220-16 are coupled to a common conductor, and electrodes 220-15 and 220-20 are coupled to a common conductor. Electrodes 220-2 through 220-4, 220-7 through 220-9, 220-12 through 220-14, and 220-17 through 220-19 are each independently coupled to their own respective conductor 222.

In some embodiments, other electrode designs can be employed to minimize the number of conductors 222 required to support the various electrodes 220. For example, a relatively large number of electrodes 220 (e.g., thirty-two, sixty-four, and greater) could be utilized on paddle 216. Electrodes 220 could be coupled to one or several electrical gates (e.g., as deposited on a flex circuit). The electrical gates can be controllably configured to couple each electrode 220 to a conductor 222 carrying cathode pulses, to couple each electrode 220 to an anode termination, or to maintain each electrode 220 at a high impedance state. The electrical gates could be controlled using a main controller, such as a logic circuit, on the paddle 216 that is coupled to a data line conductor 222. The data line conductor 222 communicates signals from an IPG that identify the desired electrode states, and the main controller responds to the signals by setting the states of the electrical gates as appropriate.

In another embodiment, a cathode conductor line 222 and an anode conductor line 222 are provided in one or several lead bodies along with a plurality of optical fibers. The optical fibers are used to carry optical control signals that control the electrode states. Specifically, paddle 216 includes photodetectors (e.g., photodiodes) that gate connections to anode conductor line 222 and cathode conductor line 222. The use of optical fibers to carry optical control signals may be advantageous, because the diameter of optical fibers suitable for such functionality is smaller than electrical conductors 222. Therefore, a larger number of electrodes 220 (as compared to using a separate electrical conductor 222 for each electrode 220) can be independently controlled while maintaining the lead body diameters at an acceptable size.

Terminals 218 and electrodes 220 are preferably formed of a non-corrosive, highly conductive material. Examples of such material include stainless steel, MP35N, platinum, and platinum alloys. In one embodiment, terminals 218 and electrodes 220 are formed of a platinum-iridium alloy. Each conductor 222 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, one embodiment uses conductors 222 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of representative embodiments, such insulative material protects an individual conductor 222 if its respective sheath 224 is breached during use.

In addition to providing the requisite strength, flexibility, and resistance to fatigue, conductors 222 formed of multi-strands of drawn-filled tubes, in accordance with the above description, provide a low resistance alternative to other materials. Specifically, a stranded wire, or even a coiled wire, of approximately 60 cm and formed of MP35N or stainless steel or the like may have a measured resistance in excess of 30 ohms. In contrast, for the same length, a wire formed of multi-strands of drawn-filled tubes could have a resistance less than 4 ohms.

Sheaths 224 and paddle 216 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of paddle lead 210, and insulate adjacent terminals 218 and/or electrodes 220. Additional structure (e.g., a nylon mesh, a fiberglass substrate) (not shown) can be internalized within paddle 216 to increase its overall rigidity and/or to cause paddle 216 to assume a prescribed cross-sectional form.

Paddle 216 may be fabricated to possess a substantially flat profile. Alternatively, paddle 216 may have an arcuate profile. In the embodiment shown in FIG. 3, wing structures 232 are formed on each longitudinal side of paddle 216. Wing structures 232 may be formed for the purpose of retaining paddle 216 within the central portion of the epidural space. In some embodiments, one or more electrodes 220 may be disposed on wing structures 232.

While a number of material and construction options have been discussed above, it should be noted that neither the materials selected nor the construction methodology is critical to the systems and methods described herein.

Figure 4:
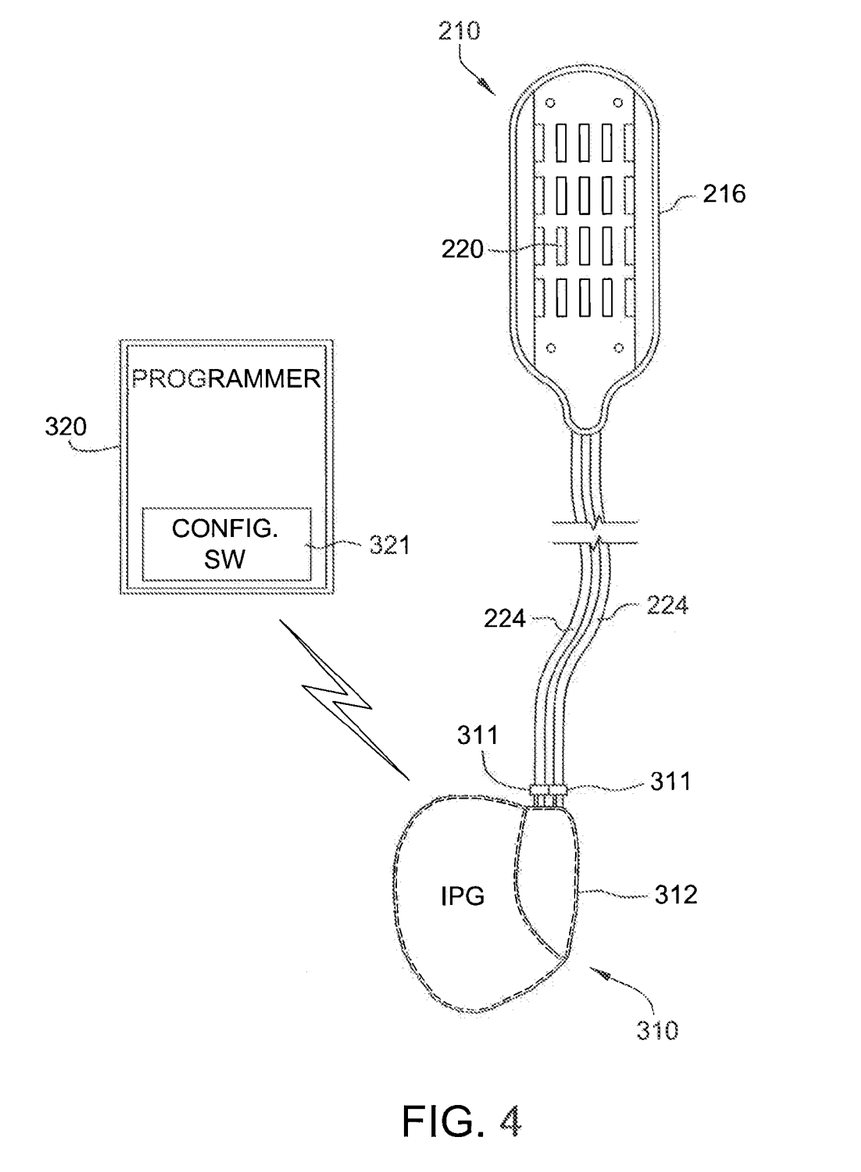
FIG. 4 is a schematic diagram of a paddle lead coupled to an implantable pulse generator in communication with a wireless programmer device according to one embodiment.

FIG. 4 depicts paddle lead 210 coupled to an IPG 310 which is in wireless communication with a programmer device 320. An example of a commercially available IPG is the Eon™ Rechargeable IPG from St. Jude Medical, Inc. (Plano, Tex.), although any suitable IPG, such as RF powered devices, could be alternatively employed. As shown in FIG. 4, paddle lead 210 is coupled to header ports 311 of IPG 310. Each header port 311 electrically couples respective terminals 218 (shown in FIG. 3) to a switch matrix (not shown) within IPG 310.

The switch matrix selectively connects the pulse generating circuitry (not shown) of IPG 310 to terminals 218, and, hence to electrodes 220. A sealed portion 312 of IPG 310 contains pulse generating circuitry, communication circuitry, control circuitry, and a battery (not shown) within an enclosure to protect the components after implantation within a patient. The control circuitry may comprise a processing device, a microprocessor, one or more ASICs, and/or any suitable circuitry for controlling the pulse generating circuitry, as described herein. The control circuitry controls the pulse generating circuitry to apply electrical pulses to the patient via electrodes 220 of paddle 216 according to multiple pulse parameters (e.g., pulse amplitude, pulse width, pulse frequency, etc.). Electrodes 220 are set to function as cathodes or anodes or set to a high-impedance state for a given pulse according to the couplings provided by the switch matrix. The electrode states may be changed between pulses.

When paddle lead 210 is initially implanted within the patient, a determination of the set(s) of pulse parameters and the electrode configuration(s) that may effectively treat the patient's condition is made. The determination or programming typically occurs through a physician's interaction with configuration software 321 executed on programmer device 320. Accordingly, programmer device 320 functions as a processing device. Configuration software 321 steps the physician through a number of parameters and electrode configurations based on a trolling algorithm. In some embodiments, the electrode configurations are stepped through by laterally "steering" the electrical stimulation by moving the anodes and/or cathodes along a row of the paddle. The patient provides feedback to the physician regarding the perceived stimulation that occurs in response the pulse parameters and electrode configuration(s). The physician may effect changes to the parameters and electrode configuration(s) until optimal pulse parameters and electrode configuration(s) are determined. The final pulse parameters and configurations are stored within IPG 310 for subsequent use. The pulse parameters and configurations are used by IPG 310 to control the electrical stimulation provided to the patient via paddle lead 210. Although single channel IPGs have been described according to some embodiments, multiple current or voltage source IPGs could alternatively be employed.

Figure 5:
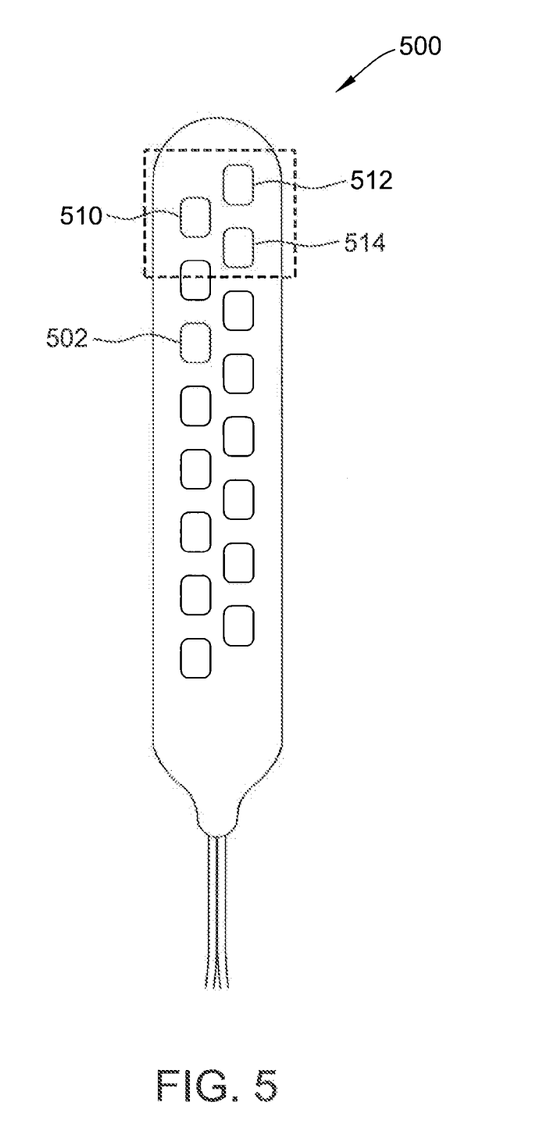
FIG. 5 is a schematic diagram of a paddle according to one embodiment.

FIG. 5 is a schematic diagram of a paddle 500 that may be used with, for example, the system shown in FIG. 4. Unless otherwise indicated, paddle 500 operates substantially similar to paddle 210 (shown in FIG. 4). Paddle 210 includes a plurality of electrodes 502. Specifically, in the embodiment shown in FIG. 5, paddle 210 includes sixteen electrodes 502 oriented in a first column and a second column that is vertically offset with respect to the first column. In other embodiments, paddle 500 may include any number and/or orientation of electrodes 502 that enables paddle 500 to function as described herein.

Local impedance measurements at electrodes 502 may be used to facilitate minimizing power consumption of paddle 500, as described herein. These impedance measurements may be used to set initial stimulation parameters (e.g., amplitude, frequency, etc.) and/or to modify parameters over time. For example, in neuromodulation systems, several electrodes 502 may be placed outside the epidural region at the same time to facilitate optimal pain relief and paraesthesia coverage. At least some of these electrodes 502 may be used simultaneously. If local impedances at electrodes 502 are known, stimulation parameters for each electrode 502 may be adjusted to facilitate minimizing an amount of energy used by paddle 500. Further, by measuring local impedances in paddle 500, lead dislodgement and fibrosis may also be detected, as described herein. For example, if local impedances for a given configuration increase significantly, stimulation using that configuration may be less effective and relatively inefficient. Further, if local impedances for a given configuration decrease significantly (e.g., due to complete dislodgement), stimulation using that configuration may be entirely ineffective, wasting energy and applying stimulation to regions that are not targeted for treatment. In both situations, using the systems and methods described herein, paddle 500 can switch to a new configuration to mitigate such issues.

Combined impedances between three different electrodes 502 may be used to calculate the local impedance at a given electrode 502. For example, the combined impedances between a first electrode 510, a second electrode 512, and a third electrode 514 may be utilized to calculate the individual impedances of each electrode 510, 512, and 514, as described herein.

More specifically, bipolar impedance measurements between two electrodes 502 (e.g., first electrode 510 and second electrode 512) predominantly measure the local impedance at the site of each of the two electrodes 502, rather than tissue impedance between the electrodes 502 (See, e.g., U.S. Patent Publication No. 20120035495 entitled "SYSTEMS AND METHODS FOR EXPLOITING NEAR-FIELD IMPEDANCE AND ADMITTANCE FOR USE WITH IMPLANTABLE MEDICAL DEVICES", which is incorporated herein by reference). Therefore, an impedance measured between electrode A and electrode B (indicated by $Z_{AB}$) can be represented as the sum of the impedance at electrode A ($Z_A$) and the impedance at electrode B ($Z_B$).

Figure 6:
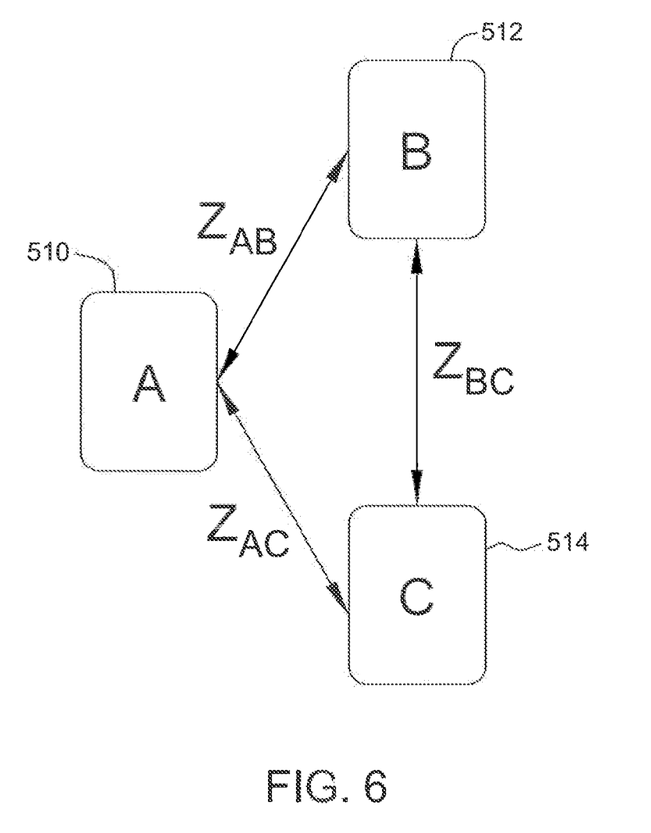
FIG. 6 is a diagram that illustrates calculating local impedances for three electrodes on the paddle shown in FIG. 5.

As shown in FIG. 6, in order to calculate an impedance at an electrode 502, impedance is measured between three electrodes 502 (e.g., first electrode 610 electrode A), second electrode 512 (i.e., electrode B), and third electrode 514 (i.e., electrode C)), also referred to as a trio of electrodes 502. Notably, any three electrodes 502 may be used, and electrodes 502 need not be proximate or adjacent to one another on paddle 510. The bipolar impedances between the three electrodes 502 can be represented by the following three equations: $Z_{AB}=Z_A+Z_B$, $Z_{BC}\ Z_B+Z_C$, and $Z_{AC}=Z_A+Z_C$. Solving these three equations simultaneously yields the following: $Z_A=0.5*(Z_{AB}\ Z_{AC}-Z_{BC})$, $Z_B=0.5*(Z_{AB}+Z_{BC}-Z_{AC})$, and $Z_C=0.5*(Z_{BC}+Z_{AC}-Z_{AB})$. Therefore, the local impedance at each electrode 502 may be calculated using the three bipolar impedance measurements between electrodes 502.

In some embodiments, to facilitate increasing an accuracy of the calculated local impedance for an electrode 502, the local impedance may be calculated using multiple trios of electrodes 502. For example, if a system includes six electrodes (e.g., electrodes A, B, C, D, E, and F), the local impedance for A may be calculated using multiple trios (e.g., ABC, ACD, AEF, etc.). For each trio, the calculated impedance, $Z_A$, may be slightly different. Accordingly, the impedances calculated for each trio may be averaged to obtain a final calculated impedance value. In one embodiment, the local impedance of an electrode of interest is calculated for every possible trio that includes the electrode. Alternatively, the local impedance of the electrode of interest is calculated for a predetermined number of trios (e.g., four trios) that include the electrode of interest.

In the example embodiment, the local impedances are calculated using IPG 310 and/or programmer device 320. The calculated impedances of electrodes 502 may be utilized in several ways, as described herein.

For example, in one embodiment, a physician and/or patient may identify a zone or region (e.g., the left half or the right half of paddle 500) that is generally effective in providing beneficial therapy to the patient. The physician and/or patient may identify or select the zone using, for example, programmer device 320. Once the zone has been identified, IPG 310 and/or programmer device 320 determines which electrodes 502 are included in the zone, and calculates the local impedances at each electrode 502 in the zone using the methods described above. Based on the calculated impedances, stimulation using electrodes 502 may be adjusted. For example, IPG 310 and/or programmer device 320 may compare the calculated impedances, and automatically cause stimulation to occur using electrodes 502 having a lowest impedance within a predefined range of impedances. The predefined range of impedances may be, for example, a range defined by approximately 400+/−200 ohms. By performing stimulation using electrodes 502 having the lowest impedance, the power consumption of paddle 500 may be reduced, improving the longevity of paddle 500 without comprising the efficacy of the therapy. Further, information identifying the electrodes 502 having the lowest impedance may be provided to the physician and/or patient via the programmer device 320.

In another embodiment, instead of identifying a zone on paddle 500, the physician and/or patient may identify a particular set of electrodes 502 using, for example, programmer device 320. Similar to above, local impedances for the selected electrodes 502 can be calculated, and IPG 310 and/or programmer device 320 may compare the calculated impedances and automatically cause stimulation to occur using electrodes 502 having a lowest impedance within the predefined range of impedances.

Whether the user specifies a zone or a particular combination of electrodes 502, the impedance may be measured continuously or periodically. Accordingly, stimulation parameters may be repeatedly modified over time based on the most recently calculated impedance values. For example, if migration (i.e., movement) of paddle 500 causes electrodes 502 to move closer to or further from the surrounding tissue, the local impedances will likely change, and the programming (i.e., the stimulation parameters) can be automatically updated. In some embodiments, stimulation may only be applied on an as-needed basis. Accordingly, in such embodiments, the local impedances may only be calculated at one time, prior to delivering stimulation. In another embodiment, paddle 500 and/or IPG 310 may be able to detect changes in a posture of the patient, and the local impedances may be calculated each time a posture change is detected.

In some embodiments, a user may not initially specify a zone or configuration of electrodes 502. Instead, IPG 310 and/or programmer device 320 may calculate local impedances for all electrodes 502 on paddle 500. Based on the calculated impedances, IPG 310 and/or programmer device 320 determines the electrode(s) 502 with the lowest impedance and recommends to a user (e.g., by displaying information on programmer device 320) that those electrode(s) 502 be used for stimulation.

Figure 7:
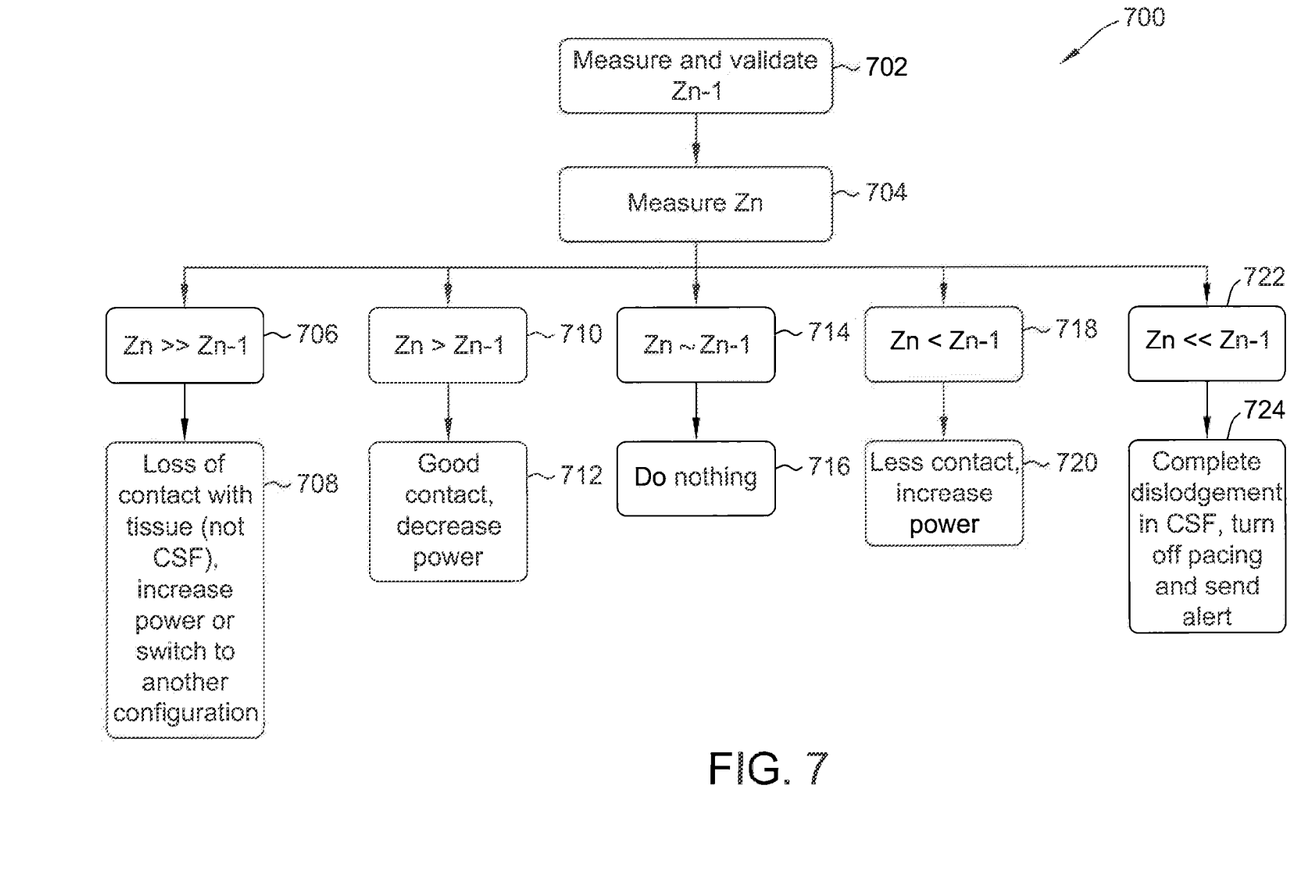
FIG. 7 is a flow diagram for controlling stimulation based on calculated local impedances.

FIG. 7 is a flow diagram 700 for controlling stimulation at a given electrode 502 based on calculated impedances. In the embodiments described herein, the calculated impedance values may be stored, for example, in memory on IPG 310 and/or programmer device 320. Accordingly, the calculated impedance values may be tracked over time, and information (e.g., graphs) indicating trends in the calculated impedance may be displayed, for example, on programmer device 320. The calculated impedance value data may also be transmitted to and processed by one or more additional computing systems.

In flow diagram 700, at block 702, an initial local impedance value, $Zn-1$, is measured (i.e., calculated) and validated for electrode 502. In some embodiments, $Zn-1$ is be a running average of several previous values, instead of a single measurement. At a later time, at block 704, a current local impedance value, $Zn$, is measured for electrode 502. Based on a comparison between the initial local impedance value $Zn-1$ and the current local impedance value $Zn$, different actions may be taken.

For example, at block 706, if $Zn$ is much greater than $Zn-1$ (e.g., more than 200 ohms greater), it indicates that electrode 502 has likely lost contact with tissue (although has not been completely dislodged into the cerebrospinal fluid (CSF)). Accordingly, flow proceeds to block 708, and the amplitude of stimulation to electrode 502 may be increased in order to keep effective therapy, or another electrode configuration will be utilized for effective stimulation.

At block 710, if $Zn$ is greater than $Zn-1$ (e.g., between 50 and 200 ohms greater), it indicates good contact between electrode 502 and the surrounding tissue. Accordingly, flow proceeds to block 712, and the power to electrode 502 may be decreased. In some embodiments, the power decrease to electrode 502 is proportional to the impedance difference between $Zn$ and $Zn-1$.

At block 714, if $Zn$ is substantially equal to $Zn-1$ (e.g., within 50 ohms), it indicates relatively little, if anything, has changed between the two measurements, and flow proceeds to block 716, where no action is taken.

At block 718, if $Zn$ is less than $Zn-1$ (e.g., between 50 and 200 ohms less), it indicates decreased contact between electrode 502 and the surrounding tissue. Accordingly, flow proceeds to block 720, and the amplitude of stimulation to electrode 502 may be increased. In some embodiments, the amplitude of stimulation increased to electrode 502 is proportional to the impedance difference between $Zn$ and $Zn-1$.

At block 722, if $Zn$ is much less than $Zn-1$ (e.g., more than 200 ohms less), it indicates that electrode 502 has likely been completely dislodged into the CSF. Accordingly, flow proceeds to block 724, and the power to electrode 502 is discontinued. Further, in this embodiment, an alert is generated to notify the physician and/or patient of the dislodgement. The alert may be any audio and/or visual indication that notifies a user, and may be communicated to the user via programmer device 320.

As noted above, the calculated local impedance of an electrode 502 may be tracked over time. Trends in the calculated local impedance may be indicative of different phenomena. For example, a gradual, continuous increase in the local impedance over time may indicate fibrosis and/or the forming of scar tissue. Accordingly, if IPG 310 and/or programmer device 320 detects a gradual increase in the local impedance over time for a particular electrode 502, programmer device 320 may communicate an alert to a user notifying the user of the potential occurrence of fibrosis and/or the forming of scar tissue.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for applying neurostimulation to a patient, the system comprising:
a paddle lead comprising a plurality of electrodes; and
an implantable pulse generator (IPG) electrically coupled to the paddle lead and configured to:
calculate, using a processing device, an impedance for each electrode in a set of electrodes on the paddle lead, by measuring an impedance between each pair of electrodes in a trio of electrodes in the set of electrodes;

determine, using the processing device, at least one electrode in the set of electrodes having a lowest impedance within a predefined range; and automatically cause the paddle lead to perform stimulation using the at least one electrode; and a programmer device communicatively coupled to the IPG and configured to control operation of the IPG.

2. The system of claim 1, wherein to calculate an impedance for each electrode, the IPG is configured to:

measure a first impedance between a first electrode and a second electrode of the trio of electrodes;

measure a second impedance between the second electrode and a third electrode of the trio of electrodes;

measure a third impedance between the third electrode and the first electrode of the trio of electrodes; and calculate, based on the first, second, and third impedances, a first electrode impedance, a second electrode impedance, and a third electrode impedance.

3. The system of claim 1, wherein to calculate an impedance for each electrode, the IPG is configured to:

calculate multiple instances of an impedance value for a particular electrode, wherein each instance of the impedance value is calculated using a different trio of electrodes that includes the particular electrode; and average the multiple instances of the impedance value to determine an impedance for the particular electrode.

4. The system of claim 1, wherein the programmer device is configured to receive a user input that identifies the set of electrodes.

5. The system of claim 1, wherein the programmer device is configured to receive a user input that identifies a zone on the paddle lead that includes the set of electrodes.

6. The system of claim 1, wherein the IPG is further configured to:

store, in a memory device, at least one previously calculated impedance value for a selected electrode;

compare, using the processing device, a current calculated impedance value for the selected electrode with the at least one previously calculated impedance value; and control an amount of power supplied to the selected electrode based on the comparison.

7. The system of claim 6, wherein the IPG is further configured to:

detect, based on the comparison, a continuous increase in the impedance of the selected electrode that is indicative of scar tissue formation; and generate a user alert in response to the detection.

8. An implantable pulse generator (IPG) configured to be electrically coupled to a paddle lead that includes a plurality of electrodes, the IPG comprising:

a memory device; and a processing device communicatively coupled to the memory device, the processing device configured to:

calculate an impedance for each electrode in a set of electrodes on the paddle lead, by measuring an impedance between each pair of electrodes in a trio of electrodes in the set of electrodes;

determine at least one electrode in the set of electrodes having a lowest impedance within a predefined range; and automatically cause the paddle lead to perform stimulation using the at least one electrode.

9. The IPG of claim 8, wherein to calculate an impedance for each electrode, the processing device is configured to:

receive a measurement of a first impedance between a first electrode and a second electrode of the trio of electrodes;

receive a measurement of a second impedance between the second electrode and a third electrode of the trio of electrodes;

receive a measurement of a third impedance between the third electrode and the first electrode of the trio of electrodes; and calculate, based on the first, second, and third impedances, a first electrode impedance, a second electrode impedance, and a third electrode impedance.

10. The IPG of claim 8, wherein the processing device is configured to receive, from a programmer device, a signal that identifies the set of electrodes.

11. The IPG of claim 8, wherein the processing device is configured to receive, from a programmer device, a signal that identifies a zone on the paddle lead that includes the set of electrodes.

12. The IPG of claim 8, wherein the processing device is further configured to:

store, in the memory device, at least one previously calculated impedance value for a selected electrode;

compare a current calculated impedance value for the selected electrode with the at least one previously calculated impedance value; and adjust an amplitude of stimulation delivered to the selected electrode based on the comparison.

13. The IPG of claim 12, wherein the IPG is further configured to:

detect, based on the comparison, a continuous increase in the impedance of the selected electrode that is indicative of scar tissue formation; and generate a user alert in response to the detection.

14. A method for applying neurostimulation to a patient, the method comprising:

electrically coupling a paddle lead to an implantable pulse generator (IPG), wherein the paddle lead includes a plurality of electrodes;

calculating, using a processing device, an impedance for each electrode in a set of electrodes on the paddle lead, by measuring an impedance between each pair of electrodes in a trio of electrodes in the set of electrodes;

determining, using the processing device, at least one electrode in the set of electrodes having a lowest impedance within a predefined range; and automatically causing the paddle lead to perform stimulation using the at least one electrode.

15. The method of claim 14, wherein calculating an impedance for each electrode comprises:

measuring a first impedance between a first electrode and a second electrode of the trio of electrodes;

measuring a second impedance between the second electrode and a third electrode of the trio of electrodes;

measuring a third impedance between the third electrode and the first electrode of the trio of electrodes; and calculating, based on the first, second, and third impedances, a first electrode impedance, a second electrode impedance, and a third electrode impedance.

16. The method of claim 14, further comprising receiving, from a programmer device communicatively coupled to the IPG, a signal that identifies the set of electrodes.

17. The method of claim 14, further comprising receiving, from a programmer device communicatively coupled to the IPG, a signal that identifies a zone on the paddle lead that includes the set of electrodes.

18. The method of claim 14, further comprising displaying, on a programmer device communicatively coupled to the IPG, information that indicates which electrode is the at least one electrode.

19. The method of claim 14, further comprising:
- storing, in a memory device, at least one previously calculated impedance value for a selected electrode;
- comparing, using the processing device, a current calculated impedance value for the selected electrode with the at least one previously calculated impedance value; and
- adjusting an amplitude of stimulation delivered to the selected electrode based on the comparison.

20. The method of claim 19, further comprising:
- detecting, based on the comparison, a continuous increase in the impedance of the selected electrode that is indicative of scar tissue formation; and
- generating a user alert in response to the detection.

* * * * *